(12) United States Patent
Sullivan

(10) Patent No.: US 7,904,315 B2
(45) Date of Patent: Mar. 8, 2011

(54) RULES-BASED HEALTH CARE REFERRAL METHOD AND SYSTEM

(76) Inventor: Robert J. Sullivan, Savannah, GA (US)

( * ) Notice: Subject to any disclaimer, the term of this patent is extended or adjusted under 35 U.S.C. 154(b) by 1287 days.

(21) Appl. No.: 11/035,645

(22) Filed: Jan. 14, 2005

(65) Prior Publication Data

US 2005/0159983 A1 Jul. 21, 2005

Related U.S. Application Data

(60) Provisional application No. 60/536,877, filed on Jan. 16, 2004.

(51) Int. Cl.
*A61B 5/00* (2006.01)
*G06F 19/00* (2006.01)
(52) U.S. Cl. ............ 705/3; 705/2; 705/4; 705/8; 705/9; 600/300
(58) Field of Classification Search .................. 705/2–4, 705/8, 9; 600/300
See application file for complete search history.

(56) References Cited

U.S. PATENT DOCUMENTS

| 5,911,132 | A * | 6/1999 | Sloane ............................. 705/3 |
| 2002/0026329 | A1 * | 2/2002 | Saito et al. ....................... 705/3 |
| 2003/0069754 | A1 * | 4/2003 | Weeks et al. ...................... 705/2 |
| 2003/0208391 | A1 * | 11/2003 | Dvorak et al. .................... 705/8 |
| 2005/0209885 | A1 * | 9/2005 | Lamb et al. ....................... 705/2 |

* cited by examiner

*Primary Examiner* — Gerald J. O'Connor
*Assistant Examiner* — Linh Michelle Le
(74) *Attorney, Agent, or Firm* — John R. Crossan; Crossan IP Law, LLC

(57) ABSTRACT

An Internet-based system and method facilitates interactive placing and acceptance of patient referrals within a health care community. A referring health care provider accesses the proposed specialty clinic or other provider through the system, identifies the patient and pertinent medical conditions, and responds to interactive queries put by the system to qualify the patient and his or her medical condition for the referral. The system automatically accepts or rejects the referral, proposes prior tests or treatments for the patient before another referral attempt is made, or accepts the referral subject to tests being completed. Accepted referrals are then scheduled by staff depending on their urgency as indicated in the interactive querying system. Rules governing the interactive querying are set by physicians and managers of the community and can be changed as conditions warrant. Security of patient information in the system in accordance with federal HIPPA requirements is readily provided via passwords and user log-ins.

17 Claims, No Drawings

RULES-BASED HEALTH CARE REFERRAL METHOD AND SYSTEM

Priority of my provisional U.S. application Ser. No. 60/536,877, filed Jan. 16, 2004, is claimed, under 35 USC §120.

FIELD OF THE INVENTION

The present invention relates to methods and systems for referring matters from one provider or supplier to another across enterprises; in a health system, it relates more specifically to patient referrals between and among health care providers such as doctors, clinics, technical service providers, and the like.

BACKGROUND OF THE ART

Referrals from general health care providers to specialists must often be made in the modern health care system. Such referrals have been done by telephone or by prescription slips, sending patients from one provider to another with long waits for appointments even when critical care was needed. Referrals were often incorrect and done for incorrect reasons, without proper documentation and/or follow-up to see that proper care was available to or was obtained by particular patients.

As healthcare providers assemble multi-enterprise based health systems to serve people in their communities, particularly for example the poor, the uninsured, and the underinsured, the size and scope of operations places unique new demands on their people, their processes and, unfortunately, their patients. The use of hand written referrals, sent by fax, couriers, and mail are required to bridge across the various information systems and operating policies and procedures inherent in any cross enterprise operation. As providers examine methods to improve these operations, they continue to focus on these three key essentials:

Access to care
Continuity of care
Quality of care

The present methods of handling referrals in such a health-care system allow a number of problems to amass.

Many of specialty clinics have significant overloads of patients. At the same time, significant numbers of the patients in the appointment books are in the wrong place, or have a low clinical need (or "acuity"), while many other patients who truly need the skills of the resource are unable to get timely appointments.

Patients arrive without complete workup information available to the specialist. Today's system, too often, relies more on "who you know" rather than on the pure clinical facts of the case. Many times, patients must wait far too long to get appropriate medical treatment.

The lack of consistent feedback to referring physicians and of convenient routing processes breaks down the continuity of care. In too many cases, specialists become primary care physicians for the patients.

Problems amplify as one moves geographically and structurally away from a health care community's traditional main campus. Community clinics, both intra-enterprise and extra-enterprise, must deal with extensive delays in obtaining an appointment for their patients (regardless of the lead times of the clinics). Clinics have the extra burden of communicating the appointment to the patient long after they have left the provider's office. Adding to the problem is the fact that the appointment was made with no patient input; hence the appointments are often not suitable for the patient. These factors contribute greatly to the exorbitant "no show" rates experienced across many health systems, particularly public systems.

Current operational approaches wind up holding a large unscheduled backlog of referral orders, with some referrals being as much as 9-12 months old. Many of these patients need relatively basic care, but they are in an "out of sight/out of mind" status with their health care providers.

In building an effective referral system, addressing just the transporting of referrals as by implementing Internet order entry alone provides little improvement to the process. A method to address a range of needs is required. These needs include:

Insuring that proper workups are done before the consultation
Defining and creating prerequisite orders for various diagnostic tests
Communicating the appropriate "best practice" protocol for healthcare
Insuring that first level providers are taking all the steps they can before referring
Confirming that the order is directed to the appropriate clinic
Determining the level of clinical need or acuity
Supporting various levels of urgency In the healthcare industry, physicians are the only individuals who have the full knowledge required to define clinical rules that can best accomplish these goals. However, physicians are not trained to develop rules in a manner that a programmer can use to transfer the rule into XML or similar computer code. A standardized method of documentation is required to bridge the gulf between the medical and information technology worlds.

SUMMARY OF THE INVENTION

It is an object of this invention to use the power of the Internet and of personal computers and servers connected to the Internet to facilitate and streamline patient referral processes among health care providers, improving and providing appropriate levels of care within the health care systems. A rules-based patient referral system is disclosed, wherein a referring provider must qualify a patient and the patient's medical conditions, test results, and the like before the referral is accepted by the referred-to provider. The rules are applied sequentially and interactively as the referral is being made, and if added tests or information are needed from the referring level, or prior to the referral visit, then they can be ordered and obtained before the visit to the second provider occurs.

According to the invention, the Internet is used to communicate among terminals of health care providers in a community and across enterprises, using secure communications methods and protocols. A provider who needs a patient to receive specialized tests, evaluations, and/or treatment goes on-line into the referral system of invention and, through the applicable rule, connects with a specific second provider, whether a physician, clinic, laboratory, technician, or the like. The patient and his or her medical condition are qualified for a visit to the referred-to provider through a series of rules-based questions put interactively to the referring provider. If the referral is appropriate then an appointment is made immediately; if added tests or information are needed then they are ordered automatically for results to come in time for the appointment. If the referral is not appropriate, the referring provider is advised of why and what alternatives appear suitable. Records are kept of each attempted referral, for administration of the system and the providers in the community, subject to federal and local confidentiality and security requirements.

The specific rules are subject to constant testing and revision, so that if problems or opportunities appear they can be dealt with or implemented without disrupting the operation of the referral system. Urgent need cases can be handled within the system or marked for special handling manually, supported by the system.

At the end of the specification is an XML-format document that defines the programming language specifications into which rules are assembled for incorporation into one, preferred embodiment of the invention.

THE PREFERRED EMBODIMENTS

As the invention was initially developed for use in public healthcare, this description of its implementation and uses are specific to a public health system. However, the invention is intended for application outside the public health system as well.

In order for the invention to function in the intended manner, XML rules containing admission criteria must be designed, usually by cooperation between the healthcare provider and a consultant. These rules provide the sole method of this embodiment for the system of the invention to determine clinical need, or acuity, of a patient for particular treatments.

The rule documentation method designed for this system, is used to guide healthcare providers to visualize their rule construction options. The method permits a knowledgeable health care consultant to draw out the full range of ideas, and it serves as an iterative tool in the development or modification of any referral rule.

One example of this implementation of the method of the present invention is as follows:

Department: MEDICINE
Division: PULMONARY
Clinic: ASTHMA CLINIC

RULE # 1071-02-0602
ASTHMA CLINIC ORDERING RULES

Orderable: REFERRAL TO ASTHMA CLINIC
PREREQUISITES TO ACCEPT A REFERRAL ORDER

1. Is the patient at least 16 years of age?
   - Yes  Continue to #2
   - No   Referral order is rejected. "Referral to Asthma Clinic is inappropriate due to patient's age. Please refer this patient to Pediatrics Comprehensive Care."

2. Has the patient been in a hospital or emergency room for asthma in the past year?
   - Yes  Was the last visit to a hospital or emergency room within the past month?
     - Yes  Referral order is accepted. "Patient should be seen within 7 to 10 days post ER or hospital. If schedule is unavailable please contact the Referral Support Center."
     - No   Referral order is accepted. "Patient will be scheduled on a next available basis."
   - No   Continue to #3

3. Please indicate the primary reason for your referral.

Poorly controlled asthma
   Medication side effect or concerns
   Question of diagnosis
   Restricted drug access One of these reasons must be selected to continue. Based upon which selection is made, a separate decision tree (below) will be provided to the physician.

POORLY CONTROLLED ASTHMA

1. Is the patient on inhaled corticosteroids?
   - Yes  Continue to #2
   - No   Rejected order. "Referral to Asthma Clinic is inappropriate at this time. Please consider placing patient on this treatment."

2. Have you completed an assessment of patient compliance?
   - Yes  Continue to #3
   - No   Rejected order. "Referral to Asthma Clinic is inappropriate at this time. Please assess the patient's compliance."

3. Is the patient on at least a medium dosage of the corticosteroid inhaler?
   - Yes  Has the patient been given 2$^{nd}$ line therapy? (long acting β agonist, theophylline, ipratropium bromide)
     - Yes  Referral order is accepted. "Patient should be scheduled in a normal fashion."
     - No   Reject order. "Referral to Asthma Clinic is inappropriate at this time. Please consider placing patient on second-line treatment appropriate to his clinical circumstances. Please consult www.pier.acponline.org and other sources.""
   - No   Reject order. "Referral to Asthma Clinic is inappropriate at this time. Please consider increasing the patient's corticosteroid inhaler dosage."

QUESTION OF DIAGNOSIS

1. Has the patient had a spirometry?
   - Yes  Did spirometry support a diagnosis of asthma?
     - Yes  Reject order. "Referral to Asthma Clinic is inappropriate at this time. Please consult www.pier.acponline.org and other sources."
     - No   Referral order is accepted. "Patient should be scheduled in a normal fashion."
   - No   Reject order. "Referral to Asthma Clinic is inappropriate at this time. Please conduct spirometry before placing this order."

-continued

RESTRICTED DRUG ACCESS

1. Are you trying to obtain these drugs due to poorly controlled asthma?

- Yes  Go to POORLY CONTROLLED ASTHMA rule #1
- No   Are you referring due to intolerance of standard (inhaled corticosteroids) therapy?
  - Yes  Is your patient using a spacing device?
    - Yes  Referral order is accepted. "Patient should be scheduled in a normal fashion."
    - No   Reject order. "Referral to Asthma Clinic is inappropriate at this time. Please give the patient a spacing device and instruct on appropriate use."
  - No   Does patient exhibit any of the following?
         Exercise induced bronchospasm
         Aspirin intolerant
         Asthma and nasal polyps
    - Yes (any box checked)
         Referral order is accepted. "Patient should be scheduled in a normal fashion."
    - No (no box checked)
         Reject order. "Referral to Asthma Clinic is inappropriate at this time. Suggest a phone consultation with Pulmonary or Allergy Specialist."

MEDICATION SIDE EFFECT

Is patient currently exhibiting medication side effects?

- Yes  Referral order is accepted. "Patient should be scheduled in a normal fashion."
- No   Reject referral order. "Referral to Asthma Clinic is inappropriate. Any concerns should be addressed by primary care."

This method of yes-no/multiple choice questions of this invention is one that physicians easily understand and can quickly and effectively work with. The same documentation method, when paired with the rule programming specifications set forth below, allows anyone familiar with XML programming to code rules that will interface with the operational system code of the invention.

The invention is to be used by all providers in the patient referral process. At the beginning of a referral lifecycle, the invention is used by the referring provider to place and to track outbound patient referrals. Once a referral is entered and accepted it is directed to a work queue at the referred-to clinic, where it awaits processing. Work queue administrators in the specialty care clinics access the work queues and schedule the referrals based on their clinical priority. The specific schedule details are entered into an Internet referral information system of the invention that performs automatic notification back to the ordering provider and the patient, as well as reminder notices to the patient. The method of communication can include email, fax, printed notices, or any known Interactive Voice Response system (IVR).

On the day of the patient appointment, clinic staff accesses the daily referrals for use by their physicians before the consultation. Specialty clinic administrators, referring site managers, and hospital administrators use reporting functions in the system of the invention throughout this process to track and measure the referral process.

In compliance with federal HIPPA regulations, users are required to log into the computers operating the system of the invention using a unique username and alphanumeric password. The invention relies on a role-based authorization control (RBAC) security system that allows each unique username to hold one or more roles and permissions for a single username. This feature is meant to create safeguards against mistakes and abuses of the system of the invention. The roles and permissions are built to accommodate specific requirements of the health system. For example, medical residents frequently rotate through many clinics during time of their residency, so to track a referral, the name of the attending physician for the clinic that the resident is working in will also be placed on the order. This level of detail is achieved through RBAC, which identifies each resident's role in the system as 'resident' and ensures that the attending physician's name is attached to the referral.

RBAC also adjusts the menu options available when a user logs in, which options are keyed to the permissions and security levels the user holds. For example, a referring physician sees only a few options because of the way such person is intended to use the invention. A referring provider is able to manage their own information, to submit referrals, and to explore the rules. On the other hand, a user in a management role has access to these functions and also to detailed reporting features, sites, queues, and user management tools. Managers use these functions to monitor and alter user settings in the system of the invention as appropriate, for instance when a medical resident is assigned to a different practice in the hospital.

When a referring provider uses the invention to place a referral, he or she is required to select a clinic and/or procedure from a list provided. The invention includes a specific feature, a variable ordering template, which allows system managers to customize the clinics and procedures available for particular referring providers to order from. For example, the managers may want to allow a group of referring providers access only to certain specialty care clinics located in their immediate geographic area.

When a referring provider selects a clinic or procedure, the invention requests demographic information as to the patient and then presents the provider with a first corresponding rule. This rule is one created upon consultation between a specialty care physician and a consultant. The system of the invention treats the rule as data, therefore, after a rule is coded into XML and activated in the referral system of the invention, referring providers interact with the rule in a question/answer format. The way the referring provider answers these questions determines the subsequent question and the rejection or acceptance and associated clinical priority of the referral. Referring provider interaction with the rules is illustrated in the following example (the asthma rules, above, are used in this example).

The referring provider logs into the system of the invention, selects 'Asthma Clinic' from the available clinics and is then prompted by the following questions and gives the following answers:

1. Is the patient at least 16 years of age?
   YES
2. Has the patient been in the hospital or emergency room for asthma in the past year?
   YES
3. Please indicate the reason for the referral:
   Poorly controlled asthma ✓
   Medication side effect or concerns Question of diagnosis
Restricted drug access
4. Is the patient on inhaled corticosteroids?
YES
5. Have you completed an assessment of patient compliance?
YES
6. Is the patient on at least a medium dosage of the corticosteroid inhaler?
YES
7. Has the patient been given second line therapy? (long acting beta agonist, theophylline, ipratropium bromide)
YES
    result: Referral order is accepted. Patient should be scheduled in a normal fashion.
NO
    result: Referral to Asthma Clinic is inappropriate at this time. Please consider placing patient on second-line treatment appropriate to his clinical circumstances; consult www.pier.acponline.org and other sources.

Thus, as the referring provider places the referral he or she is prompted by questions that assess the clinical urgency of the referral. The questions, or admission criteria, are specific to each specialty care clinic or procedure that is available for accepting referrals. As the referring provider answers questions about the patient's condition, the next question(s) change according to the logical flow of the admission criteria. The result is similar to that of a computer-based medical consultation between two physicians. Depending on how the referring physician answers the questions, the referral will ultimately be categorized as normal, inappropriate, or into varying levels of urgency. The category that is applied to an accepted referral then affects the manner in which it is then scheduled and processed.

In addition to determining the clinical need or acuity of a referral, the rule-based system of the invention will also automatically generate referrals for any other required procedures. For example, if a patient receives an accepted referral to the Pulmonary clinic, but needs to have a current MRI before he or she is seen in the Pulmonary clinic, the system of the invention will spawn an additional order for an MRI at the time the referral to the Pulmonary clinic is placed. The invention links all the related referrals, so the referring physician and the patient are notified about the spawned order; the additional order is scheduled and processed in the same manner as an ordinary or primary referral.

When the referral is accepted by the system for the referred-to clinic, a physical document containing information specific to that referral is printed on the ordering physician's printer. In addition to the referral information, a default confirmation message, specific to the clinic and/or procedure being ordered is printed at the top of the confirmation page. Both the referral information and the default confirmation message are printed and given to the patient, as they are meant as reference tools for the patient. Physicians and administrators in each specialty care clinic use the system of the invention to create the default confirmation message. This message will consist of any text chosen by the specialty care clinic and is intended as a vehicle for communication between the clinic and the patient before the patient's appointment. This communication also will convey information pertinent to the patient's appointment, such as directions to the clinic, contact information for the clinic, and any dietary, make-up, or other restrictions for the visit.

The urgency level assigned to a referral affects how it is scheduled and processed. Every day, a healthcare provider assigned as a work queue staff accesses his or her clinic's work queue, in accordance with an additional feature of the invention. Each accepted referral resides in the work queue for the appropriate clinic or procedure and waits at most one day to be processed. When the work queue staff accesses the queue they see a list of all the referrals yet to be scheduled, ordered by urgency. The work queue staff then opens and optionally prints each referral and schedules each one based on the available appointment times in the clinic. The referrals may for instance be printed in batches of 100—a batch printing—in a large clinic. Clinic administrators and hospital management access work queue reports that detail this process, including the time used to process referrals and the number of outstanding referrals not yet scheduled.

Information regarding each referral is stored on a designated server under HIPPA-compliant security. Storing all referrals enables several features of the invention to function, including facilitating provider communication regarding referral status, patient communications regarding appointment times, and management reporting functions.

Frequently, new research and information in medicine make current practices obsolete. The system and method of the present invention contain a rules management module that allows managers to access rules and to change them to reflect changes in clinical practices and procedures. It is intended that managers will communicate with specialty care physicians to stay abreast of changes in the medical field and cooperate fully with them to make necessary changes to the rules of the invention as such changes become appropriate.

Sample Implementation of the Invention

The purpose of these specifications is to allow the creation of an object structure in an XML file that describes a decision set (rule) to the point that it can be rendered by a referral information system without any other input or data. The XML file will conform to the XML schema that will be used to insure that the description is reliable.

Conventions (See Table Below for Definitions)
    DecisionSet names will be composed of upper and lowercase characters, digits, and the hyphen. The name must start with an upper case character.
    All labels will be composed of uppercase characters, digits, and the hyphen. They must start with an alphabetic character.
    DataItems will be composed of lowercase characters, digits, and the hyphen. They must start with a lowercase character.
    Values that are to be returned by data entry or a selection will be appropriate to their datatype.
    Display values (that is, the string that is displayed to alert a user to the item that is to be completed, as opposed to the identity of the item returned by the HTML form processor) will be any valid string values.
    Each Rule must have a corresponding message to be displayed to the user. If there is no user input for a rule, the message will be ignored but by convention the message could be, NONE. This will confirm the author's intention.
    Action conditions will always denote the value of a DataItem in angular brackets, < . . . >. Since each DataItem name must be unique, it is possible to use any DataItem that has already been defined. DataItem names will also be qualified, e.g. <DataSet.DataItem>.
    An action condition that only contains a string (with no white space) will be assumed to represent the value of the current DataItem, which implies that the current DataSet only contains one DataItem.

In the following table, IRIS is the inventor's Internet Referral Information System, operating according to the invention.

| Element | Description |
| --- | --- |
| | Description |
| DecisionSet | This is the container for the all of the data pertaining to a specific decision set. It will have the following attributes: |
| | attribute      description |
| | Name      A string containing the name of the set. |
| | Completed      YES if the definition is complete<br>NO if the definition is incomplete (this allows authors to save incomplete work but will notify IRIS that it is not ready to be tested). |
| | metadata      Author, date, version, etc. |
| Rule | This is modeled as an abstract class in Java and an abstract type in XML. Each DecisionSet must have at least one rule. |
| | attribute      description |
| | label      A string that must be unique among all labels. The special string, START, is reserved for the first Rule. Each label aside from START must have at least one corresponding Action.label associated with it. |
| | message      A string that represents a message that is to be displayed when the node is displayed for user input. In the case that there is no user activity the message will be ignored. |
| Terminal | A node that indicates the end of a decision process. A terminal either represents an order that has been selected or an error (in that the Decision Set does not have an appropriate order corresponding to the requirements the user has input). A Terminal is a concrete class or element that is inherited from Rule. |
| | attribute      description |
| | token      A string that represents an end condition. Usually this will be an order but it may be an error code as well. |
| | tokenType      ORDER represents an order and ERROR represents an error. This enumeration makes it easier for IRIS to interpret the end condition. |
| DataSet | A DataSet is a concrete class or element that is inherited from Rule. This is a container for the DataItems and Actions. DataItems and Actions will be presented in the order they are to be displayed by IRIS |
| ActionType | This represents the action (the next node to be displayed) based on a condition. The condition will be a string representing a logical condition that IRIS will evaluate to either true or false. The first expression that evaluates to true will be the one that IRIS uses to determine the next node to display. |
| | attribute      description |
| | condition      A string that can will be evaluated as either true or false based on the value of the current or previous DataSet.DataItems. |
| | label      A string that represents the unique Rule.label that is to be displayed next if the condition evaluates to true.. |
| DataItemType | This is another abstract class or element. It represents data that is entered by the user. |
| | attribute      description |
| | name      A unique string within the DataSet. |
| SimpleItemType | This is a concrete class or element that is inherited from DataItem-Type. This represents in input field that will take free text. The data type of the text will be validated by standard conventions by IRIS (though we could use regular expressions to validate these types if they start to expand). |
| | attribute      description |
| | itemValue      A string that represents the default value of this string if there is one. This will be displayed in the field for the user by IRIS when the node is selected. |
| | dataType      This is a string from one of the following: {STRING, NUMBER, DATE, BOOLEAN}. |
| | single      This only has meaning for STRING types. It defaults to YES meaning that it is a simple text field. otherwise it will represent an HTML TextArea field. |

-continued

Description

| Element | Description |
|---|---|
| SelectionType | This is a concrete class or element, which is inherited from DataItemType. This element represents either a radio or checkbox selection item. The default will be for a radio selection. In order to facilitate user interaction the author may specify that the selections be described in a tabular format where each row has several attributes displayed in columns. This will allow the author to make the selections clearer when asking for a decision that the provider may not see often. Otherwise each selection will have only one string for its description. Because of the nature of selection items, this is also a container for the individual elements in the selection group. |
| | attribute — description |
| | selectionType — RADIO (default) representing a radio selection (one item out of many) or CHECKBOX selection (one or more items from many). |
| | tabular — A NO(default) meaning there is no tabular data to display. YES means there is tabular data to display. |
| SelectedItem | A triple that describes the particular item to be selected. The attributes correspond to HTML conventions. |
| | attribute — description |
| | returnValue — A string that is returned by the HTML form if this item is selected |
| | displayValue — The value the user sees that represents this selection. This field is ignored if tabular is selected for the Selection above. |
| | default — A NO (default) meaning that this is not selected by default when IRIS displays the node. YES means it is a default. |
| Columns | In the case that tabular data is to be displayed, this provides the value for a column. The columns are assumed to be in order of the ColumnNames. |
| | attribute — description |
| | columnValue — A string representing the value to display in this column. |
| ColumnName | A string representing the heading for the column for a tabular presentation. |
| | attribute — description |
| | columnHead — A string containing the column heading |

The combination of the above documentation method and the rule programming schema (language) set forth at the end of this specification, before the claims, allows for the invention to be created and used.

RBAC should be implemented based on a clinic's existing organizational structure, keeping in mind the personnel factors, capabilities, and restrictions that may exist.

Implementation of the variable ordering template should occur before the invention is activated. It is intended that hospital administrators with control over the affected specialty care clinics and referring clinics make a determination of which services and clinics will be made available to the referring clinics. When the decision is made, a consultant sets up the initial variable ordering templates before the invention is activated. After the initial setup of the variable ordering templates the hospital managers will have full control over any future changes. It is intended that only upper level managers and hospital administrators have access to this feature as it can drastically impact demand on healthcare services.

In order for referrals to be prioritized, physician defined admission criteria in the form of rules need to be implemented in the form of questions to be posed to the referring provider. The admission criteria need to be organized into a logical format conducive to the question-answer format of the invention. The referring provider encounters and interacts with the rule at the time the referral is placed. Implementing this procedure is not difficult, as the predefined format of the XML code is designed to be used with minimal training. Providing the referring provider with a username, password, and appropriate access level are the only necessary steps to ensure interaction between the provider and the rules. The invention assumes Internet connectivity and a browser that can work with XML code.

The default confirmation messages that print with the patient's referral are, as stated above, defined by each specialty care clinic individually and can be changed at any time. Existing clinics have the ability to change their default confirmation messages at any time. The authority to change a default confirmation message for a clinic is only intended for the clinic administrator.

After a referral is scheduled, the invention provides information to the patient regarding the appointment time and location. This feature can be implemented through mail, fax, email, or the IVR and requires the patient to confirm the appointment or reschedule the appointment.

The manner in which work queue management is implemented depends greatly on the personnel resources available to a specific specialty care clinic, however there are general guidelines that must be followed. Work queues are designed with varying levels of authority that grant access to features appropriate to each level of authority. A 'work queue administrator', 'work queue manager', and 'work queue staff' need to be assigned for each clinic that will process referrals.

The 'work queue staff' has the lowest level of access and is able to process a referral, print batches, reschedule a referral, and view basic queue reports. The procedure for processing referrals begins with the work queue staff printing a batch of referrals, which for instance may come in batches of 100 referrals. Then, the work queue staff accesses the schedule for the clinic, finds an appropriate time for the referral to be handled, and schedules the appointment in accordance with the invention. At any time the work queue staff can reschedule a referral if necessary. The work queue manager has one additional responsibility in addition to the functions of the work queue staff, managing print batches. This function allows the work queue manager to reset a print batch if it printed incorrectly or was printed in error. In addition to all lower level functions, the 'work queue administrator' has the ability to add or remove people from the work queue as required.

It is intended that different people will hold each of the above-described roles in a specialty care clinic. However, due to personnel constraints, it is sometimes necessary for one person to hold several or all of these roles. The invention allows users to hold several titles at the same time to accommodate this reality. It is intended that hospital administrators measure the performance and accuracy of the admission criteria, consulting with specialty care physicians to make revisions when necessary.

In order to implement the HIPPA-compliant database, the invention needs to be stored on either a secure server, managed either by the health care facility or by a consultant. Once this is achieved, all the necessary functions that enable data warehousing of referral information occur automatically through the code in the invention, so no further implementation is required.

There is no need to implement the rules management module independently, as it is a standard feature of the invention. However, detailed processes are required for successful use of this feature. A computer-savvy consultant trains the health care managers and IT personnel to code, test, validate, and activate the rules that run in accordance with the invention. The administrators or their IT staff must also understand how to upload, download, and manage the version log of all the existing rules.

Many variations may be made in the invention as shown and its manner of use, without departing from the principles of the invention as described herein and/or as claimed as our invention. Minor variations will not avoid the use of the invention.

---

SAMPLE XML CODING

```xml
<?xml version="1.0" encoding="UTF-8"?>
<!-- edited with XMLSPY v5 rel. 3 U (http://www.xmlspy.com) by Ivan Handler (Correctional Health Technologies, Inc.) -->
<xs:schema xmlns:xs="http://www.w3.org/2001/XMLSchema" elementFormDefault="qualified" attributeFormDefault="unqualified">
    <xs:element name="DecisionSet">
        <xs:annotation>
            <xs:documentation>Container for the rules. Should always be the root</xs:documentation>
        </xs:annotation>
        <xs:complexType>
            <xs:sequence maxOccurs="unbounded">
                <xs:element ref="Rule"/>
            </xs:sequence>
            <xs:attribute name="name" use="required">
                <xs:simpleType>
                    <xs:restriction base="xs:string">
                        <xs:pattern value="(\p{Lu}(\p{L} | \p{Nd} | \- )*)"/>
                    </xs:restriction>
                </xs:simpleType>
            </xs:attribute>
            <xs:attribute name="completed" use="optional" default="NO">
                <xs:simpleType>
                    <xs:restriction base="xs:string">
                        <xs:enumeration value="NO"/>
                        <xs:enumeration value="YES"/>
                    </xs:restriction>
                </xs:simpleType>
            </xs:attribute>
            <xs:attribute name="version" type="xs:decimal" use="required"/>
            <xs:attribute name="author" type="xs:string" use="required"/>
            <xs:attribute name="site" type="xs:string" use="required"/>
            <xs:attribute name="email" type="xs:string" use="optional"/>
            <xs:attribute name="description" type="xs:string"/>
        </xs:complexType>
    </xs:element>
    <xs:complexType name="SelectedItemType" mixed="false">
        <xs:annotation>
            <xs:documentation>Represents a single item from a selection list</xs:documentation>
        </xs:annotation>
        <xs:sequence>
            <xs:element name="ColumnValue" type="xs:string" minOccurs="0" maxOccurs="unbounded"/>
        </xs:sequence>
        <xs:attribute name="returnValue" type="xs:string" use="required"/>
        <xs:attribute name="displayValue" type="xs:string" use="required"/>
        <xs:attribute name="default" use="optional" default="NO">
            <xs:simpleType>
                <xs:restriction base="xs:string">
                    <xs:enumeration value="NO"/>
                    <xs:enumeration value="YES"/>
```

SAMPLE XML CODING

```xml
            </xs:restriction>
          </xs:simpleType>
        </xs:attribute>
      </xs:complexType>
      <xs:complexType name="SelectionType" abstract="false" mixed="false">
        <xs:annotation>
          <xs:documentation>Represents a selection list</xs:documentation>
        </xs:annotation>
        <xs:complexContent mixed="false">
          <xs:extension base="DataItemType">
            <xs:sequence>
              <xs:element name="ColumnName" minOccurs="0" maxOccurs="unbounded">
                <xs:simpleType>
                  <xs:restriction base="xs:string">
                    <xs:pattern value="(\p{Lu}(\p{Lu} | \p{Nd} | \-)*)"/>
                  </xs:restriction>
                </xs:simpleType>
              </xs:element>
              <xs:element name="SelectedItem" type="SelectedItemType" maxOccurs="unbounded"/>
            </xs:sequence>
            <xs:attribute name="type" use="optional" default="RADIO">
              <xs:simpleType>
                <xs:restriction base="xs:string">
                  <xs:enumeration value="RADIO"/>
                  <xs:enumeration value="CHECKBOX"/>
                </xs:restriction>
              </xs:simpleType>
            </xs:attribute>
            <xs:attribute name="tabular" use="optional" default="NO">
              <xs:simpleType>
                <xs:restriction base="xs:string">
                  <xs:enumeration value="NO"/>
                  <xs:enumeration value="YES"/>
                </xs:restriction>
              </xs:simpleType>
            </xs:attribute>
          </xs:extension>
        </xs:complexContent>
      </xs:complexType>
      <xs:complexType name="SimpleItemType">
        <xs:annotation>
          <xs:documentation>Represents textual input (HTML text or text area)</xs:documentation>
        </xs:annotation>
        <xs:complexContent>
          <xs:extension base="DataItemType">
            <xs:attribute name="itemValue" use="required">
              <xs:simpleType>
                <xs:restriction base="xs:string">
                  <xs:whiteSpace value="collapse"/>
                </xs:restriction>
              </xs:simpleType>
            </xs:attribute>
            <xs:attribute name="dataType" use="required">
              <xs:simpleType>
                <xs:restriction base="xs:string">
                  <xs:enumeration value="STRING"/>
                  <xs:enumeration value="DATE"/>
                  <xs:enumeration value="NUMBER"/>
                  <xs:enumeration value="BOOLEAN"/>
                </xs:restriction>
              </xs:simpleType>
            </xs:attribute>
            <xs:attribute name="singleLine" use="optional" default="YES">
              <xs:simpleType>
                <xs:restriction base="xs:string">
                  <xs:enumeration value="YES"/>
                  <xs:enumeration value="NO"/>
                </xs:restriction>
              </xs:simpleType>
            </xs:attribute>
          </xs:extension>
        </xs:complexContent>
      </xs:complexType>
      <xs:complexType name="DataItemType" abstract="true">
        <xs:annotation>
          <xs:documentation>Represents a control (such as an HTML control)</xs:documentation>
        </xs:annotation>
        <xs:attribute name="name" use="required">
```

SAMPLE XML CODING

```xml
            <xs:simpleType>
                <xs:restriction base="xs:string">
                    <xs:pattern value="(\p{Ll}(\p{Ll} | \p{Nd} | \-)*)"/>
                </xs:restriction>
            </xs:simpleType>
        </xs:attribute>
</xs:complexType>
<xs:complexType name="ActionType">
    <xs:annotation>
        <xs:documentation>Branching mechanism</xs:documentation>
    </xs:annotation>
    <xs:sequence>
        <xs:element name="Condition">
            <xs:simpleType>
                <xs:restriction base="xs:string">
                    <xs:whiteSpace value="preserve"/>
                </xs:restriction>
            </xs:simpleType>
        </xs:element>
    </xs:sequence>
    <xs:attribute name="label" use="required">
        <xs:simpleType>
            <xs:restriction base="xs:string">
                <xs:pattern value="(\p{Lu}(\p{Lu} | \p{Nd} | -)*)"/>
            </xs:restriction>
        </xs:simpleType>
    </xs:attribute>
</xs:complexType>
<xs:complexType name="RuleType" abstract="true">
    <xs:annotation>
        <xs:documentation>Fundamental type</xs:documentation>
    </xs:annotation>
    <xs:sequence>
        <xs:element name="Message">
            <xs:simpleType>
                <xs:restriction base="xs:string">
                    <xs:whiteSpace value="collapse"/>
                </xs:restriction>
            </xs:simpleType>
        </xs:element>
    </xs:sequence>
    <xs:attribute name="label" use="required">
        <xs:simpleType>
            <xs:restrictionbase="xs:string">
                <xs:pattern value="(\p{Lu}(\p{Lu} | \p{Nd} | -)*)"/>
            </xs:restriction>
        </xs:simpleType>
    </xs:attribute>
</xs:complexType>
<xs:complexType name="TerminalType">
    <xs:annotation>
        <xs:documentation>End Node</xs:documentation>
    </xs:annotation>
    <xs:complexContent>
        <xs:extension base="RuleType">
            <xs:attribute name="token" type="xs:string" use="required"/>
            <xs:attribute name="tokenType" default="ORDER">
                <xs:simpleType>
                    <xs:restriction base="xs:string">
                        <xs:enumeration value="ORDER"/>
                        <xs:enumeration value="ERROR"/>
                    </xs:restriction>
                </xs:simpleType>
            </xs:attribute>
        </xs:extension>
    </xs:complexContent>
</xs:complexType>
<xs:complexType name="DataSetType">
    <xs:annotation>
        <xs:documentation>Holds input data and branches</xs:documentation>
    </xs:annotation>
    <xs:complexContent>
        <xs:extension base="RuleType">
            <xs:sequence maxOccurs="unbounded">
                <xs:sequence minOccurs="0" maxOccurs="unbounded">
                    <xs:element ref="DataItem"/>
                </xs:sequence>
                <xs:element name="Action" type="ActionType" maxOccurs="unbounded"/>
```

| SAMPLE XML CODING |
| --- |
| ```
            </xs:sequence>
          </xs:extension>
        </xs:complexContent>
      </xs:complexType>
      <xs:element name="Rule" type="RuleType">
        <xs:annotation>
          <xs:documentation>Global element and substitution head</xs:documentation>
        </xs:annotation>
      </xs:element>
      <xs:element name="Terminal" type="TerminalType" substitutionGroup="Rule">
        <xs:annotation>
          <xs:documentation>Global element can substitute for a Rule</xs:documentation>
        </xs:annotation>
      </xs:element>
      <xs:element name="DataSet" type="DataSetType" substitutionGroup="Rule">
        <xs:annotation>
          <xs:documentation>Global element can substitute for a Rule</xs:documentation>
        </xs:annotation>
      </xs:element>
      <xs:element name="DataItem" type="DataItemType">
        <xs:annotation>
          <xs:documentation>Global element and substitution head</xs:documentation>
        </xs:annotation>
      </xs:element>
      <xs:element name="SimpleItem" type="SimpleItemType" substitutionGroup="DataItem">
        <xs:annotation>
          <xs:documentation>Global element can substitute for a DataItem</xs:documentation>
        </xs:annotation>
      </xs:element>
      <xs:element name="Selection" type="SelectionType" substitutionGroup="DataItem">
        <xs:annotation>
          <xs:documentation>Global element can substitute for a DataItem</xs:documentation>
        </xs:annotation>
      </xs:element>
</xs:schema>
``` |

I claim as my invention:

1. An interactive clinical-rule based patient referral management system designed using "client/server" architecture to optimize a process flow for cross enterprise operations, as in a health system, the system operating on electronic data-processing equipment and via a global communications network which interconnects a plurality of service providers across a community, the network comprising a plurality of input/output terminals and links among them, and the system carrying out steps of:

employing at least one set of clinical rules for making and allowing a patient referral between first, referring and second, referred-to health care providers, each said set of clinical rules being adapted to interact with the first provider for automatically checking the proposed referral against the content of said clinical rules for acceptance or refusal of said referral for the second provider, said clinical rules being applicable to the medical appropriateness of the proposed referral, and the clinical rules providing for sequentially querying the referring provider through dynamic branching based on the responses made;

receiving data input to a terminal of said first, referring provider, the data comprising a proposed referral of a particular patient to said second provider, the proposed referral providing clinical information about the patient and the medical conditions prompting the proposed referral;

the system being adapted to automatically check the proposed referral against said clinical rules for acceptance or refusal of the referral by the second provider; and the system being adapted to allow or refuse the referral based on the patient's clinical information, medical conditions, and answers stated in view of the applicable clinical rules.

2. The system of claim 1, the system configured such that if the referral is allowed to the second provider, the system automatically advises at least one of the referring provider and the patient of an appointment time and date as accepted by the second provider.

3. The system of claim 1, wherein the sequential querying according to the applicable clinical rules is performed by the system as the referral order is being placed, by establishing an interactive dialog between the first provider and the applicable clinical rule which will result in allowance, redirection, or refusal of the proposed referral as soon as a result is apparent from the responses to the sequential queries.

4. The system of claim 1, wherein a record is created and maintained in a computer memory of each referral proposed in the system and of its disposition, including the identities of the referring and referred-to providers and the medical conditions stated.

5. The system of claim 1, wherein the system assures compliance with applicable requirements as to patient privacy and information security.

6. The system of claim 1, wherein the clinical rules are tested and revised in the light of expectations and experience of providers using the system on an on-going basis.

7. The system of claim 1 wherein, when the interactive dialog between the first provider and the clinical rules determines existence of clinical acuteness of a patient's medical condition, a proposed referral is flagged with an urgent status and each such proposed urgent referral is routed through a separate processing work path for prompt handling.

8. The system of claim 1, wherein the system is adapted to automatically spawn an additional order, related to the original order but processed separately, for a diagnostic test required for the second provider to most effectively diagnose and treat the patient without requiring additional data entry by or from the first, referring provider.

9. The system of claim 1, wherein the system further treats the clinical rules as data in the system and engages each applicable clinical rule at the time of placement of the proposed referral by the first provider.

10. The system of claim 1, wherein each of several users of the system may undertake and perform any of multiple user roles required to perform specified tasks while maintaining one username for each of said several users.

11. The system of claim 1, wherein a variable ordering template is employed to customize available referral options for the referring provider.

12. The system of claim 1, wherein information regarding the disposition of each entered referral is communicated to the referring provider and to the patient.

13. The system of claim 1, wherein referrals are directed by the system to predetermined work queues for the appropriate clinics or procedures so the referrals may be scheduled and processed by work queue staff.

14. A method for referring patients in a health care community among health care providers therein for meeting different specific clinical needs of the patients, the method comprising the steps:

establishing an interactive patient referral system and network communicating within the community between and among input and output terminals accessible by each of said providers;

creating a series of interactive clinical queries operating on and through said terminals for each of a number of referral possibilities within said community, each clinical query having at least two set responses, and each query response leading automatically to one of another clinical query, an allowance of the referral, a rejection of the referral as proposed, and a redirection to a different service at the same or a different servicing location; and advising automatically both the referring provider and the patient of any success of the referral, including at some point a confirmation of an appointment date, time, and place as accepted by the referred-to provider.

15. The patient referral method of claim 14, further comprising the step of creating said interactive clinical queries by cooperation between medical service providers and system managers, and further updating the clinical rules as medical practices and knowledge are advanced.

16. The patient referral method of claim 14, further comprising the step that permanent records of each referral attempt are maintained in the system, whether the referral is successful or not, and wherein such records include the identity of at least one of the referring provider, the patient, and the service sought to be ordered.

17. The patient referral method of claim 14, further comprising the step of customizing the clinical queries permitted to certain of the referring providers via use of a variable ordering template.

\* \* \* \* \*